United States Patent [19]

Lombardo et al.

[11] 4,318,480
[45] Mar. 9, 1982

[54] METHOD AND APPARATUS FOR POSITIONING THE POINT OF DROPLET FORMATION IN THE JETTING FLUID OF AN ELECTROSTATIC SORTING DEVICE

[75] Inventors: Igino Lombardo, Sharon; W. Peter Hansen, Middleboro, both of Mass.

[73] Assignee: Ortho Diagnostics, Inc., Raritan, N.J.

[21] Appl. No.: 68,113

[22] Filed: Aug. 20, 1979

[51] Int. Cl.³ .................................... B07C 5/342
[52] U.S. Cl. .................... 209/3.1; 209/579; 209/906; 250/222 PC; 346/75; 364/413; 356/72; 361/226
[58] Field of Search ............... 209/3.1–3.3, 209/571, 579, 906, 127 R; 250/222 R, 222 PC; 356/39, 72, 73, 335, 338; 361/226; 364/413; 346/75

[56] References Cited

U.S. PATENT DOCUMENTS

| | | | |
|---|---|---|---|
| 3,380,584 | 4/1968 | Fulwyler | 209/3 |
| 3,710,933 | 1/1973 | Fulwyler et al. | 209/3.1 |
| 3,761,941 | 9/1973 | Robertson | 346/1 |
| 3,769,627 | 10/1973 | Stone | 346/75 |
| 3,826,364 | 7/1974 | Bonner et al. | 209/3.1 |
| 3,836,912 | 9/1974 | Ghougasian et al. | 346/75 |
| 3,851,169 | 11/1974 | Faxvog | 250/222 |
| 3,878,519 | 4/1975 | Eaton | 346/1 |
| 3,907,429 | 9/1975 | Kuhn et al. | 356/28 |
| 3,920,702 | 10/1975 | Corll | 356/72 |
| 3,941,479 | 3/1976 | Whitehead | 356/102 |
| 3,953,860 | 4/1976 | Fukimoto et al. | 346/75 |
| 3,963,606 | 6/1976 | Hogg | 209/3 |
| 3,982,251 | 9/1976 | Hochberg | 346/75 |
| 4,025,926 | 5/1977 | Fujimoto et al. | 346/1 |
| 4,045,770 | 8/1977 | Arnold et al. | 346/75 |
| 4,047,183 | 9/1977 | Taub | 346/75 |
| 4,148,718 | 4/1979 | Fulwyler | 209/3.1 |

OTHER PUBLICATIONS

Chen et al., "Feedback for Synchronized Pressure Jet Using Optical Sensor"; IBM Tech. Discl., vol. 16, No. 12, 5-74.
"Laser Flow Microphotometry for Rapid Analysis and Sorting of Mammalian Cells", Mullaney et al., Annals New York Academy of Sciences, vol. 267, pp. 176-190.
"Feedback for Synchronized Pressure Jet Using Optical Sensor", IBM Technical Disclosure Bulletin, vol. 16, No. 12, May 1974, pp. 3877-3878.
"Phase Detection on Ink Jet Droplets", IBM Technical Disclosure Bulletin, vol. 16, No. 3, Aug. 1973, p. 880.

Primary Examiner—Joseph J. Rolla
Attorney, Agent, or Firm—Audley A. Ciamporcero, Jr.

[57] ABSTRACT

A novel method for positioning the point of droplet formation in the jetting fluid of an electrostatic sorting device is disclosed. The formation of the uniform droplets is carried out via the application of vibrational energy imparted by a transducer to a jetting laminar flow stream. Previously sensed particles contained within the core portion of the laminar stream are subsequently sorted from the stream as part of a subsequently formed droplet. The disclosed method uses the dependency of the droplet formation point on the amplitude of the wave form applied to the transducer and the modulation of this amplitude to control the droplet formation point distance. The position of the droplet formation point is detected via the use of a light source and photodetector focused on the jetting stream at the position at which the droplet formation point is to be located, and a method for automatically maintaining the breakpoint at that position is described.

13 Claims, 4 Drawing Figures

METHOD AND APPARATUS FOR POSITIONING THE POINT OF DROPLET FORMATION IN THE JETTING FLUID OF AN ELECTROSTATIC SORTING DEVICE

CROSS REFERENCE TO RELATED APPLICATIONS

The present application is related to the following applications, each of which is assigned to the assignee of the present application and are hereby incorporated by reference as if fully set forth herein: The invention of Igino Lombardo, Donald E. Barry, and W. Peter Hansen entitled, "Method For Detecting And Controlling Flow Rates Of The Droplet Forming Stream Of An Electrostatic Particle Sorting Apparatus", Ser. No. 068,231, filed Aug. 20, 1979; the invention of Igino Lombardo and Donald E. Barry entitled, "Automatic Relative Droplet Charging Time Delay System For An Electrostatic Particle Sorting System Using A Relatively Moveable Stream Surface Sensing System", Ser. No. 068,259, filed Aug. 20, 1979; the invention of Igino Lombardo and Donald E. Barry entitled, "Method For Automatically Setting The Correct Phase Of The Charge Pulses In An Electrostatic Flow Sorter", Ser. No. 068,234, filed Aug. 20, 1979; the invention of Donald E. Barry and Igino Lombardo entitled, "A Method For Measuring The Velocity Of A Perturbed Jetting Fluid In An Electrostatic Particle Sorting System", Ser. No. 068,235, filed Aug. 20, 1979; and the invention of Richard A. Dussault and Igino Lombardo entitled, "A Servo System To Control The Spatial Position Of Droplet Formation Of A Fluid Jet In A Cell Storing Apparatus", Ser. No. 068,112, filed Aug. 20, 1979.

As to Ser. No. 068,231, please see generally pages 15-25; as to Ser. No. 068,259, see generally pages 15-22; as to Ser. No. 068,234, see generally pages 15-21; as to Ser. No. 068,235, see generally pages 15-22; and as to Ser. No. 068,112, see generally pages 15-27.

BACKGROUND OF THE INVENTION

The present invention relates generally to the field of electrostatic flow sorters, and more particularly to those sorters which are adapted to sense the presence and/or character of particles in a laminar flow stream and to selectively sort those particles by breaking that stream into a number of discrete droplets, and sorting those droplets containing such preselected particles. Such sorters are known for use in sorting and analyzing cellular compositions of given biological samples, as for example in the counting/analysis of cell types for a given blood sample.

In an apparatus of this general type, laminar flow is established through an area at which a light scattering, florescence or volume measurement is taken. Once a cell of interest has been sensed, an electronic time delay is normally activated for the length of time required for the cell to cover the distance from the point of cell detection to the point of droplet formation. Droplet formation may be accomplished by vibrating a flow chamber or orifice through which the stream passes, at a frequency sufficient to cause droplet formation, usually on the order of about 40,000 cycles per second. When a cell of interest arrives at the droplet formation point, a charging pulse may be applied to charge the droplet (plus, minus, or neutral) so that as the droplet of interest enters a subsequent DC field, it may be deflected as desired for collection. A general overview of this technique is provided in "Laser Flow Microphotometry For Rapid Analysis And Sorting Of Mammalian Cells", Mullaney, et al, Annals New York Academy Of Sciences, Vol. 267, pages 176-190 (see in particular, pages 180 and FIGS. 3 and 4).

Such particle sorters are also disclosed in U.S. Pat. Nos. 3,710,933 (Fulwyler, et al) and 3,380,584 (Fulwyler) and 4,148,718 (Fulwyler). In these patents, sorting is accomplished in accordance with a selected parameter which may be size, volume, presence of radioactivity, color, florescence, light absorption or any quality capable of being translated into an electrical quantity. These patents additionally disclose single or multi parameter measurements to effect such sorting.

In order to selectively sort those droplets containing cells which are determined to be of particular interest, apparatus of this general type generally depends upon a flow rate estimate for the fluid containing a particular cell. This flow rate estimate is used to estimate the time between cell detection and the droplet breakpoint, at which selective charging of the droplet to be sorted takes place. As disclosed in U.S. Pat. No. 3,710,933, such systems are normally aligned and adjusted prior to taking cell measurements. In particular, droplet formation is normally checked by illuminating the emerging liquid jet near the flow chamber with a strobe light or equivalent light source. The strobe light is synchroflashed with respect to the oscillator frequency. Droplet formation can then be viewed using a microscope, and by varying the voltage and frequency applied to the stream perturbing transducer, droplet formation can be adjusted for a given nozzle diameter and flow rate. See U.S. Pat. No. 3,710,933, Column 11, lines 14-49.

As described particularly in U.S. Pat. No. 3,710,933, (Fulwyler, et al), by pressurizing various reservoirs with known pressures, flow rates can be estimated and cell flow rate adjusted by varying the relative pressures between the various reservoirs feeding into the flow stream. The approximate time delay between cell sensing and droplet formation (which is estimated in Fulwyler, et al to be in the order of 1400 microseconds) can be estimated so that an appropriate droplet charging generator will operate in combination with a pulse height analyzer and cell separation logic to charge the selected cell containing droplets for subsequent electrostatic sorting.

A number of factors affect the ability of a given apparatus to selectively sort one or more types of target cells from a continuous cell stream. Even assuming that the detection equipment for identifying each cell to be sorted is 100% accurate, differences in flow rate, temperature, fluid viscosity, and transducer performance can affect the time delay or location of the desired target-cell-containing droplets at the breakpoint, which is the point at which a charge pulse must be administered to insure that the target cell will be subsequently electrostatically sorted.

Heretofore, one of the methods used to adjust such a sorting apparatus involves running a test sample through that apparatus which is set or programmed to sort for one or more readily identifiable cell types. According to this procedure, the delay time is manually adjusted until those droplets which are sorted from the flow stream are found to contain the expected number of target cells. While this method, used alone or in combination with the stroboscopic method discussed above, has achieved some success in this art, it is prone to a certain degree of error, particularly during periods of extended machine use and/or changing operating conditions, such as changing sample viscosities and/or temperatures.

In U.S. Pat. No. 3,826,364 (Bonner, et al), a particle sorting method and apparatus are disclosed wherein a coaxial flow stream is released through a vibrating nozzle. Inspection (interrogation) of the stream by one or more cell sensing means for sensing cells in the stream occurs immediately downstream of the nozzle. In the Bonner, et al device, charging pulses are supplied at appropriate times for proper separation of the drops through the use of delay units which are adjusted to provide the necessary time delay to allow for travel time of the particle from the point of particle scatter detection to the point where the stream breaks into drops. Bonner states:

"With the present arrangement the delay time between observation of a particle and its capture by a separating droplet is predictable to within three drop periods. Such high degree of predictability is due primarily to the uniform velocity of the inner particle containing stream 12A of the coaxial flow jet. That is, across the inner stream 12A the stream velocity is substantially uniform whereby particles anywhere within the cross-section of the inner stream travel with the same velocity from the point of observation to the drop separation point of the stream." U.S. Pat. No. 3,826,364, Col. 7, lines 22-32.

As further explained in the Bonner, et al disclosure, the duration as well as the time of application of the charging pulse is critical to the separation of at least the droplet containing the target particle to be sorted. After describing a preferred charging pulse which will charge at least three drops, Bonner, et al states:

"Obviously, if instrument tolerances, variations, drift and like permitted, then a drop charging time sufficient to charge only two successive drops, or a single drop, could be employed." U.S. Pat. No. 3,826,364, Col. 8, lines 2-6.

As also pointed out by Bonner, et al, a drop breaking from a given flow stream carries with it a charge which is proportional to the potential between the droplet stream and the surrounding electrodes or charging surfaces at the time the drop separates from the stream. If the drop breaks off from the jet stream during the transition time from the drop charge pulse, either during the leading or trailing edge of that pulse, some intermediate value between zero and the desired full charge may be imparted to the target droplet. In the Bonner, et al apparatus, on/off transitions of the drop charging pulse are synchronized with the drop formation means, whereby charge pulse transitions may be synchronized to occur only intermediate the formation of droplets and not when droplets separate from the stream. This is made possible in the Bonner device by the provision of a variable phase control unit included in the transducer drive circuit which is adjusted for proper timing of droplet formation with the droplet charge pulse. As with the Fulwyler devices discussed above, stroboscopic illumination of the stream permits stream viewing through a suitable microscope, the stroboscopic illumination being synchronized by the drop charging pulses such that the stream, and more particularly the deflected drops, may be illuminated to ensure that the deflected drops contain the desired particles to be sorted.

More recently, various apparatus and method have been proposed for timing the application of a charge pulse so that droplets containing the particles to be sorted may be selectively charged. In U.S. Pat. No. 3,963,606 (Hogg), a particle separator is disclosed for separating particles in a fluid according to certain particle characteristics. The Hogg device includes a means for adjusting an electrical delay to be equal to the time between the emergence of a particle from a jet forming aperture to the point of break off. Hogg proposes the use of a movable scale in place of the ground glass of prior art projection microscopes, this scale being linked to a potentiometer of an RC oscillator to thereby control the osciallator's frequency. A second potentiometer for controlling the clock oscillator frequency is coupled to a height adjustment member of the aperture, this frequency being used to clock delay shift registers such that the charging pulse may easily be made to occur at the appropriate time, irrespective of fluctuations of pressure, velocity, amplitude and frequency of the droplet forming generator. See U.S. Pat. No. 3,963,606, (Hogg) Col. 2, lines 23-36. Accordingly, Hogg represents a more automated version of the stroboscopic projection microscopic techniques discussed above.

Droplet forming characteristics in a perturbed stream have also been considered in connection with the art of ink jet printing. In the ink jet printing art, where discrete ink droplets formed in an ink jet stream are electrostatically directed to form characters on a recording surface, particular attention has been paid to establishing uniform droplet formation and charging characteristics. Since the charge imparted to any given droplet at its breakpoint is proportional to its surface area, i.e., the shape of that droplet at the breakpoint, and since even slight charge variations may produce erratic deflection characteristics, ink jet printing artisans have proposed various systems for producing an ink jet stream comprising uniformly shaped and uniformly charged droplets which will exhibit predictable down stream deflection behavior. These problems are complicated by the tendency of perturbed streams to form "satellites" which not only affect the charge imparted to preceeding or succeeding droplets, but also alter the volume of those droplets, thereby correspondingly affecting print uniformity.

In the ink jet printing art, numerous systems have been proposed for sensing the characteristics of a perturbed ink jet stream, either above or below the breakpoint of that stream. U.S. Pat. No. 3,907,429 (Kuhn, et al) discloses a method and device for detecting the velocity of droplets formed from a liquid stream. According to this disclosure, discrete droplets are directed between a pair of apertures and a light source which is strobed at a selected frequency and directed towards the apertures. By detecting the time between when a first of the apertures is blocked by a droplet in the stream as indicated by the light being broken during the strobe and the time when a second of the apertures is blocked by another droplet, when the light source is counted, the velocity of the droplets may be measured and a correction of the velocity made by changing the pressure of the manifolds supplying the liquid stream. In U.S. Pat. No. 3,769,627 (Stone) an ink jet printing system using ion charging of droplets is disclosed wherein a light source and photocell located downstream from the breakpoint of a perturbed stream is used to sense the passage of discrete droplets and to time delayed charges subsequently applied thereto. Stone states:

"Selective drop charging involves the induction of charges in the drop being formed by a surrounding charged electrode. The induced charge varies in accordance with the inducing voltage until the instant in time when the droplet physically separates from the stream. From that time on, the induced charged is trapped and remains with the drop. It is obvious, therefore, that the charging process must be carefully synchronized with the timing of the drop break off. This involves the use of complex phasing control sensors and loops. This in turn, increases the cost of the equipment. It is an object of this invention to provide an ink drop charging system which does not depend upon the synchronization of the charging with the break off time.

It is another object of this invention to produce an ink drop charging system, which charges drops after they break off from the ink jet stream." U.S. Pat. No. 3,769,627 (Stone), Col. 1, lines 18-35.

This method is accomplished by using the above-described photocell arrangement for the purpose of counting and synchronizing charges applied as discrete droplets pass a plurality of separate charging stations which respond to coded information applied to each station in synchronism with the passage of each drop.

As disclosed in U.S. Pat. No. 4,047,183 (Taub), efforts have also been made to control the formation and shape of droplets in an ink jet stream by sensing the surface wave profile of the continuous portion of the stream (upstream from the breakpoint) by illuminating that portion of the stream with a radiant energy source such as a laser. The surface wave profile produced by illuminating the stream is sensed to provide the fundamental and harmonic frequency components thereof, and a perturbation drive signal, the amplitude and relative phase of which is a function of the sensed frequency components, is provided for controlling the formation and shape of the droplets. After discussing the advantages and difficulties of controlling the break off geometry, particularly with the respect to the illumination of satellite formations, Taub discloses the practical desirability of measuring the ink jet stream upstream rather than downstream from the droplet break off point:

"The ideal time to sense the frequency, phase, and amplitude components of the ink jet stream for determining drop break off characteristics is at the precise time droplets are formed therefrom. This is usually impossible to achieve, however, since the droplets are normally formed inside the charged electrode. Therefore, according to the present invention, the drop break off characteristics are determined by sensing upstream of break off, rather than downstream as taught by the prior art. The continuous portion, that is, the portion just prior to break off of the stream is sensed to determine the break off characteristics. In response to the sensed characteristics, a piezoelectric drive signal is provided which controls droplet formation, and accordingly provides increased drop charging efficiency." U.S. Pat. No. 4,047,143 (Taub), Col. 4, lines 53-68.

Taub discloses a system wherein an ink jet manifold having a perturbation means such as a piezoelectric crystal emits a perturbed ink jet stream into charge electrode structures which are pulsed in "a well known manner" to selectively apply charge to the droplets. A source of radiant energy, which may comprise a helium-neon laser, emits radiant energy focused on the continuous portion of the jet "just prior to the jet entering the charged electrode structure". "Since the ink is opaque, a shadow is formed" which is imaged through a lens onto a substrate which has a slit formed therein. The shadow formed thereby represents the surface wave profile of the jet which is a representation of the respective amplitudes and relative phases of fundamental and harmonic frequencies. Taub states: "The light passing through the slit 44 is influenced by the wave passing a given point on the perimeter of the jet, and accordingly is a representation of the frequency components of the jet at this particular point, as well as being indicative of the shape of a given droplet when it breaks-off downstream. It is necessary to make this slit somewhat larger than the largest diameter to be measured, typically the drop diameter, so that the clipping of the wave form does not occur, as well as preventing the generation of spurious diffraction effects. A narrow band pass filter 48, which has a band pass on the order of 100A centered in the laser wavelength, is used so measurements may be made in room light. The light passed by the filter 48 is then transmitted to a photomultiplier tube 50 which measures the intensity of the light. Therefore, the output voltage of the photomultiplier tube 50 is proportional to the diameter of the jet blocking the slit, which is to say, to the local diameter of the jet at the point being probed . . . It is to be appreciated that the signal output . . . may be applied to analyzing means 80 by other timing means such as a stepping motor, or alternatively may be applied concurrently to inputs of devices 82, 84 and 86, rather than in the time sequence described." U.S. Pat. No. 4,047,183. See Col. 6, lines 27-68, Col. 7, lines 1-26.

In Taub's preferred embodiment, the output signal so obtained is conditioned to control the fundamental and harmonic frequencies applied to the piezoelectric perturbation means for controlling the droplet formation and shape of droplets produced by the ink jet stream.

For other disclosures of ink jet printing systems using optical sensors, see IBM Technical Disclosure Bulletin Volume 16, No. 12, May 1974, Page 3877-8, entitled "Feedback For Synchronized Pressure Jet Using Optical Sensor"; and IBM Technical Disclosure Bulletin, Vol. 16, No. 3, August 1973, Page 880, entitled "Phase Detection On Ink Jet Droplets".

For other disclosures relating to various ink jet printing synchronization systems, please refer to U.S. Pat. No. 4,025,926 (Fujimoto, et al) entitled, "Phase Synchronization For Ink Jet System Printer"; U.S. Pat. No. 4,045,770 (Arnold, et al) entitled, "Method and Apparatus For Adjusting The Velocity Of Ink Drops In An Ink Jet Printer"; U.S. Pat. No. 3,953,860 (Fujimoto, et al) entitled, "Charge Amplitude Detection For Ink Jet System Printer"; U.S. Pat. No. 3,761,941 (Robertson) entitled, "Phase Control For A Drop Generating and Charging System"; U.S. Pat. No. 3,836,912 (Ghougasian, et al) entitled, "Drop Charge Sensing Apparatus For Ink Jet Printing System"; U.S. Pat. No. 3,982,251 (Hochberg) entitled, "Method and Apparatus For Recording Information On a Recording Medium"; U.S. Pat. No. 3,878,519 (Eaton) entitled, "Method and Apparatus For Synchronizing Droplet Formation In A Liquid Stream".

For other patents disclosing particle or flow sorting systems, please see U.S. Pat. No. 3,941,479 (Whitehead) entitled, "Use Of Modulated Stimulus To Improve Detection Sensitivity For Signals From Particles In A Flow Chamber"; U.S. Pat. No. 3,851,169 (Faxvog) entitled, "Apparatus For Measuring Aerosol Particles"; and U.S. Pat. No. 3,910,702 (Corll) entitled, "Apparatus For Detecting Particles Employing Apertured Light Emitting Device".

SUMMARY OF THE INVENTION

The present invention provides a novel method and apparatus for precisely establishing and positioning the breakpoint of a laminar flow stream of an electrostatic particle sorting apparatus. By precisely controlling the breakpoint of this system, other factors, such as variable surface tension, viscosity, temperatures, etc. which could otherwise interfere with the appropriate charging of particle containing droplets, do not interfere with droplet charging synchronization.

A novel electrostatic particle sorting system is disclosed comprising a flow means for establishing the flow of a continuous particle containing stream, comprising at least a particle containing core stream portion and a surrounding sheath stream portion. An optical detection means is provided for optically detecting particles at least at a particle sensing point along said stream. Perturbation means for perturbing said stream with at least a preselected frequency and amplitude are disclosed for causing said stream to form a breakpoint at which said stream becomes a series of discrete droplets. In order to time said relative charging such that said selected droplets contain at least selected particles detected by the optical detection means, a synchronization means is provided comprising a sheath sensing means for sensing the light scatter and extinction character of the stream at a sheath sensing point subsequent to the locus of said perturbation; surface character analysis means for producing an output signal which is at least selectively responsive to said sheath sensing means; and perturbation amplitude adjustment means responsive to said surface character analysis means for establishing and maintaining said breakpoint at said sheath sensing point.

In the preferred embodiment, the sheath sensing means comprises a radiant energy source focused on the stream to measure the scatter and extinction of said stream, and more particularly, of the sheath stream portion of that stream. The sheath sensing means accordingly produces a surface character output signal which is proportional to the surface character of the stream. In accordance with the preferred embodiment, perturbed laminar flow streams have been found to exhibit substantially different and distinguishable output signals when they are sensed above, below or at their breakpoints. Accordingly, by comparing real time waveform characteristics with a reference wave form characteristic settings, an error signal may be generated to vary the amplitude of the transducer until the breakpoint is established and maintained at the sheath sensing point. Accordingly, assuming a fixed flow rate, a given timing delay will permit the precise droplet charging of droplets containing particles identified upstream for sorting.

Accordingly, a primary object of the present invention is the provision of an improved electrostatic particle sorting apparatus wherein the breakpoint of a perturbed laminar flow stream is established and maintained at a fixed location. This and other objects of the present invention will become apparent from the following more detailed description.

DESCRIPTION OF THE PREFERRED EMBODIMENTS

Although specific forms of the invention have been selected for illustration in the drawings, and the following description is drawn in specific terms for the purpose of describing these forms of the invention, this description is not intended to limit the scope of the invention which is defined in the appended claims.

The present invention is intended for use with an electrostatic particle sorting apparatus wherein a series of particles suspended in a fluid are introduced within a sheath stream 12 to create a laminar flow stream 14. This stream is then caused to flow through a laminar flow chamber within which an optical detection means detects particles at least at a particle sensing point, and distinguishes which of those particles are to be sorted from the stream. This optical detection may comprise the use of a helium neon laser focused on the laminar flow stream 14 within the laminar flow chamber. By using various photo-optic detectors in combination with various dyes introduced in the core stream, the scatter, absorption, florescence or other characteristics of the particles sensed at the particle sensing point may identify those particles for subsequent sorting.

Figure 1:
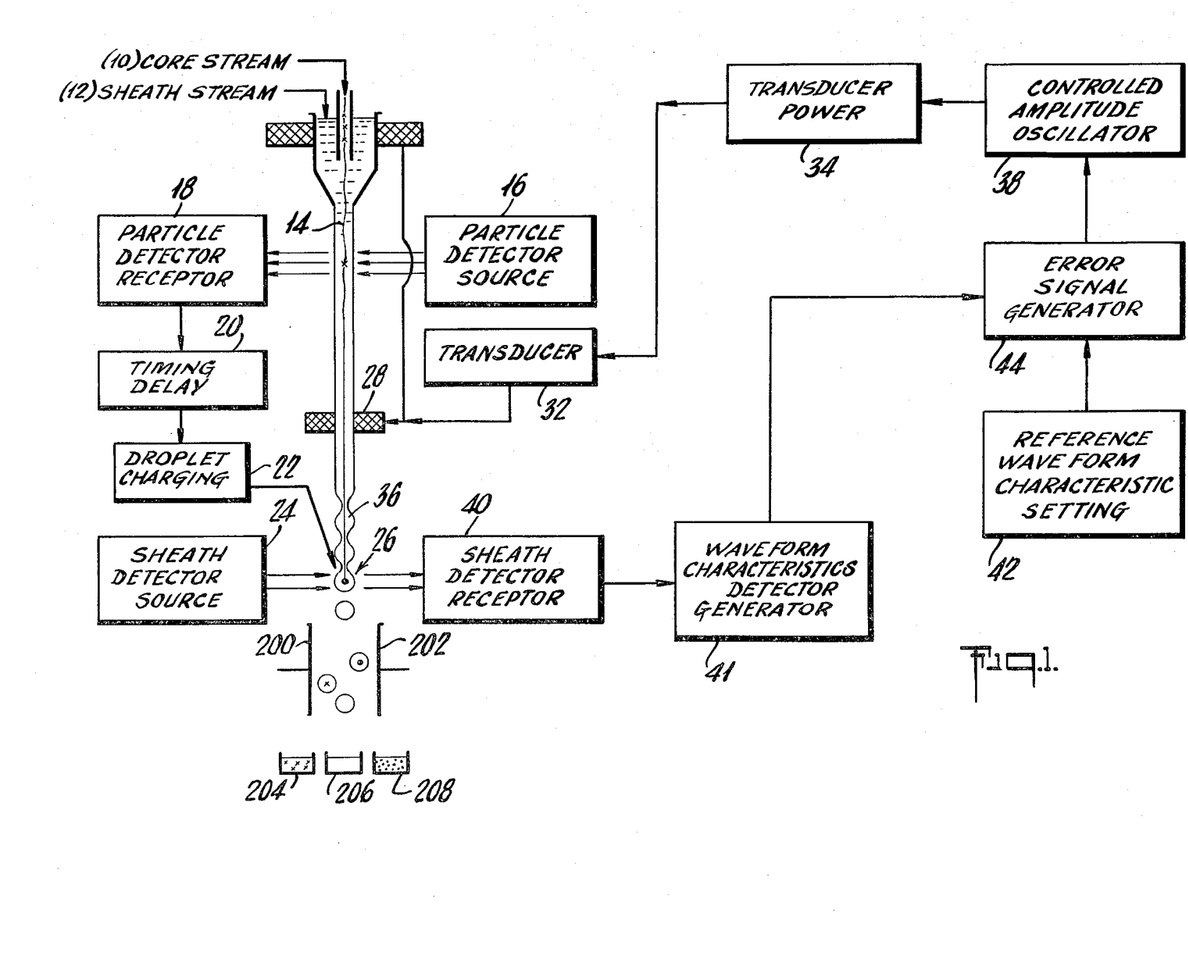
FIG. 1 is a diagrammatic hybrid block drawing of the preferred embodiment apparatus of the present invention.

The particle detector source 16 may be a light source, a light emitting diode, helium neon laser, or laser diode. One or more particle detector receptors 18 may be oriented at one or more positions with respect to the stream, depending upon the particular type and location of energy to be detected. In the event that a particle selected for sorting has been sensed, an appropriate timing delay circuit 20 adjusted for triggering the droplet charging circuit 22 will cause the relative charging of the droplet containing the preselected particle precisely at the time that that droplet is formed at the breakpoint 26. Following the detection of the desired particle at the particle sensing point 30, the laminar flow stream issues through an orifice 28 which is perturbed by a transducer and transducer driver 32 and 34 respectively. The perturbations in the perturbed laminar flow stream 36 gradually increase in size or amplitude due to the surface tension of the jetting liquid. In accordance with the preferred embodiment of the present invention, the perturbation means, which comprises the transducer 32, transducer driver 34 and controlled amplitude oscillator 38, perturb the stream with at least a preselected frequency and amplitude to cause the stream to form a breakpoint designated generally 26.

The synchronization means of the present invention comprises a sheath sensing means for sensing the light scatter and extinction character of the stream at a sheath sensing point subsequent to said perturbation and for producing a surface character output signal which is proportional thereto. As shown in FIG. 1, the sheath sensing point and the breakpoint correspond, the breakpoint being automatically maintained at the sheath sensing point, as described more fully hereinafter. The sheath sensing means comprises a sheath detector source 24, which is a source of radiant energy with respect to which the sheath stream portion is essentially translucent. In the preferred embodiment, the sheath detector source may be a helium neon laser, a light emitting diode, a laser diode, or a conventional light source. The sheath detector source is focused on the stream. Suitable optics should be provided for the purpose of focusing the radiant energy upon the stream. A lens assembly comprising two cylindrical lenses has been found to be suitable for this purpose, each of these lenses having their axis oriented perpendicular to the axis of incident light, as well as perpendicular with respect to each other. It has been found suitable to utilize a front cylindrical lens having a focal length of approximately 6 mm and a back lens having a focal length of approximately 11 cm. The preferred sheath detector receptor is a photodiode, but may also be a photomultiplier. Of the above-identified lenses, the front lens tends to focus the radiant energy upon the stream, while the back lens focuses incident energy towards the diode. It has been found suitable to use a conventional FC200 Ortho Instruments' lens assembly for this purpose. This lens assembly may, for example, be placed approximately ¼ inch from the flow stream, and the photodiode placed approximately 1 inch on the opposite side of the stream past the point of focus on the lens assembly for the purpose of permitting the photodiode to pick up a substantial portion of the light neither scattered nor extinguished by the stream, but not so much light as to permit detector saturation.

In order to measure the relative scatter and extinction of the stream at the sheath detection point, a sheath detection receptor 40 is located on the opposite side of the stream in a position such that the relative differences in the scatter of the sheath stream will cause proportional differences in the output of the sheath detector receptor, which output represents a surface character output signal. In the preferred embodiment, the sheath detector receptor is a photodiode or, less preferably, a photomultiplier.

The surface character output signal is received by a waveform characteristics detector generator 41 which analyze the surface character of the stream and produces its own output signal which is compared to the signal of a reference waveform characteristic setting 42 via an error signal generator 44 to produce an error signal in the event that the droplet breakpoint is found not to be at the sheath sensing point. This error signal will increase or decrease the amplitude or perturbation applied to the laminar flow stream by the transducer by acting through the aforementioned controlled amplitude oscillator 38 and transducer driver 34. In this manner, the droplet breakpoint designated generally 26 will automatically be relocated to the sheath sensing point and will be maintained in that position even in the event that other factors such as surface tension, viscosity, flow rate, temperature, orifice diameter etc. vary during the operation of the device. In the preferred embodiment, for a given laminar flow stream, the sheath sensing point should be located so that under normal conditions the transducer amplitude is set at about 30% of its maximum amplitude, thereby permitting substantial adjustment of the amplitude in order to compensate for the above-described effects.

Figure 2:
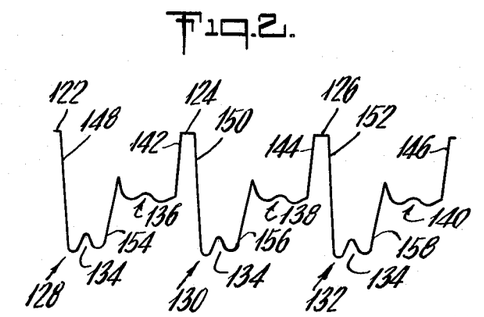
FIG. 2 is a representative waveform of a surface character output signal produced at the breakpoint region of a laminar flow stream.
Figure 3:
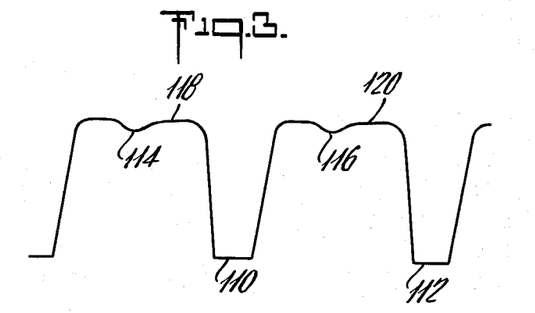
FIG. 3 is the waveform of the surface character output signal when the sheath sensing point is located below the breakpoint of a perturbed laminar flow stream.
Figure 4:
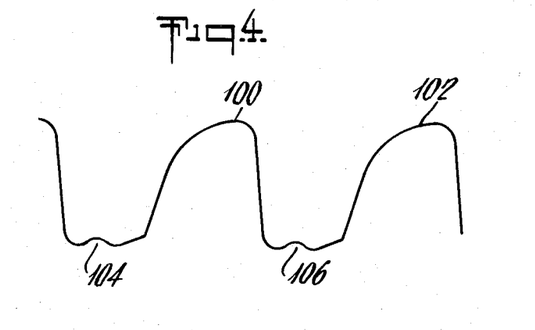
FIG. 4 is the waveform of the surface character output signal produced when the sheath sensing point is located above the breakpoint of a perturbed laminar flow stream.

Referring now to FIGS. 2, 3, and 4, representative waveforms are illustrated for the laminar flow stream at, below and above the breakpoint, respectively. As monitored by the sheath sensing means, real time proceeds from left to right while the amount of light sensed by the sheath detector receptor increases vertically. Referring first to FIG. 4, which is a representative trace of the perturbed laminar flow stream 36 when the sheath sensing point is located substantially above the breakpoint, the surface character output signal will be seen to be substantial sinusoidal. Peaks 100 and 102 correspond to relatively thinner portions of the perturbed stream wherein significantly lesser proportions of the radiant energy emitted by the sheath detector source 24 are caused to scatter, and thus substantially greater portions of that energy are received by the sheath detector receptor 40. Conversely, troughs 104 and 106 correspond to "bulges" or areas of relatively greater amplitude in the perturbed laminar flow stream 36, and correspondingly cause substantially greater portions of the radiant energy from the sheath detector source 24 to be scattered, and thus not received by the sheath detector receptor 40. Referring now to FIG. 3 which is a surface character output signal when the sheath sensing point is located substantially below the breakpoint, that is, when discrete droplets have already been formed, each of the troughs 110 and 112 correspond to discrete droplets, slight troughs 114 and 116 to small intermediate "satellites", and the remainder of the waveform, 118 and 120, when peak amounts of light are received by the sheath detector receptor, to the spaces between droplets (and/or satellites). The unique waveform shown in FIG. 2 is the wave form of the surface character output signal when the sheath sensing point and breakpoint region correspond. The spaces between droplets 122, 124, and 126 represent times when maximum amounts of light are collected by the photodiode sheath detector receptor 40. The deepest troughs, designated generally 128, 130, and 132, represent the maximum bulge of the droplet to be formed. Small ripples 134 are seen to be formed in the bulge, and may be the result of harmonics in the transducer frequency, or otherwise may naturally result from the behavior of droplets at the breakpoint, which behavior is not yet fully understood. Following the bulge but still connected thereto are ligament portions which represent the rapid stretching of the tail of the bulge into a ligament which has a smaller center than ends. This ligament size and geometry blocks only about one half the light as the largest portion of the droplet. This ligament portion has broken from the proceeding drop, and thus steep ligament slopes 142, 144, and 146 are evident leading to the free air spaces, such as 124 and 126, between droplets. It will be seen from the waveform at FIG. 2 that three particularly steep slopes of significant amplitude comprise the waveform at breakpoint. First, negative drop forming slopes 148, 150, and 152, positive drop/ligament slopes 154, 156, and 158, and positive ligament ending slopes 142, 144, 146. This may be contrasted with the slopes exhibited by the waveforms illustrated in FIGS. 3 and 4 wherein even numbers of positive and negative slopes are observed.

In accordance with the preferred embodiment of the present invention, a certain degree of ambient light may also be collected by the sheath receptor detector, and accordingly, troughs 110, 112, 104, and 106 are slightly flattened instead of uniformly rounded, as would be expected if ambient light were excluded from the system. Additionally, it has been found that the breakpoint waveform in FIG. 2 need not be as well defined as is illustrated in that figure, but rather distinctive breakpoint waveforms may nonetheless be derived even if a slight defocusing of the sheath receptor source is permitted, thereby eliminating detection of the small ripples, such as ripples 134 and/or some of the particular details of the ligament shapes, as illustrated at 136, 138 and 140.

As recognized by one of ordinary skill in this art, small satellites such as those represented at 114 and 116 of FIG. 3 are extremely unstable, possible due in part to their travelling in the wake of much larger spherical objects and/or other behavior caused by differential induced charges between adjacent charges. It is theorized that the shape of air flow around the larger spherical object will tend to move the satellite droplets either up or down depending upon the size, wave length and flow rate of the droplet stream. Accordingly, the waveform shown in FIG. 3 would be expected to be produced within approximately three wave lengths away from the breakpoint. As the sheath detection point is moved down, the effects of drag and flow around the sphere will become more evident, and the satellites distinguished as either "fast" or "slow" satellites. In the event, for example, that satellite 116 is a "fast" satellite, it would tend to merge with its proceeding drop and accordingly would be seen to shift generally towards drop 110 until it merged therewith. Similarly, if satellite 116 were a "slow" satellite, its position will tend to shift relative toward drop 112 until it merged and was consumed by drop 112, which is the succeeding drop relative to that satellite.

In accordance with the preferred embodiment of the present invention, the wave form characteristics detector generator will analyze the surface character output signal for the purpose of determining whether that signal compares favorably with a reference wave form characteristics setting signal. While one of ordinary skill in this art will recognize from the differences in wave forms set forth in the figures that there are many parameters which could be used to distinguish the wave form of FIG. 2 from those of FIGS. 3 and 4. It is presently believed that the technique disclosed in the related application of Richard A. Dussault and Igino Lombardo entitled, "A Servo System To Control The Spacial Position Of Droplet Formation Of A Fluid Jet In A Cell Sorting Apparatus" is the best way of accomplishing this analysis. As more fully described in this related application, by differentiating the surface character output signal, an odd number of spikes corresponding to the three steep breakpoint spikes of substantial amplitude will be produced when the sheath sensing point is located at the breakpoint, whereas an even number of such spikes will be produced per cycle if the sheath sensing point is located either above or below the breakpoint. In either of these latter two cases, the error signal generator will produce an error signal to vary the controlled amplitude osciallator and thus will act through the transducer driver 34, the transducer 32, and orifice 28 to vary the perturbation amplitude of perturbed laminar flow stream 36. This in turn will move the breakpoint of the perturbed laminar flow stream until that breakpoint corresponds to the sheath sensing point, at which time no further error signal, and thus no further change in transducer amplitude need be effected. Assuming a constant flow rate, a fixed time delay produced by timing delay 20 will effect droplet charging through droplet charging circuitry 22 such that droplets charged at the breakpoint may be sorted through the application of an electric field created by deflection plates 200 and 202, such that the desired particles to be selected may be gathered in one of the sample collection vessels 204, 206, or 208.

From the above it will be seen that an extremely simple, yet effective method and apparatus are disclosed for precisely determining an establishing the breakpoint of a perturbed laminar flow stream at a fixed distance from the particle detection point. Assuming a fixed flow rate, an appropriate fixed timing delay will accordingly ensure precise droplet charging of droplets containing particles to be sorted.

It will be understood that various changes in the details, materials and arrangement of parts which have been herein described and illustrated in order to explain the nature of this invention may be made by those skilled in the art within the principle and scope of the invention as expressed in the following claims. As used herein, "perturbed" or "perturbation" is meant to include not only mechanical/vibratory methods for creating discontinuities in the stream, but also discontinuities which are induced by other means such as alteration of stream surface tension, for example, by electrical, thermal, or optical means. Likewise, periodic or aperiodic perturbations are meant to be included.

It will further be understood that the "Abstract of the Disclosure" set forth above is intended to provide a non-legal technical statement of the contents of the disclosure in compliance with the Rules of Practice of the United States Patent and Trademark Office, and is not intended to limit the scope of the invention described and claimed herein.

What is claimed is:

1. An electrostatic particle sorting system, comprising:
   (a) flow means for establishing the flow of a continuous particle containing stream comprising at least a particle containing core stream portion and a surrounding sheath stream portion, said stream having a particle sensing point defined therealong;
   (b) particle sensing means for optically detecting said particles at least at said particle sensing point;
   (c) perturbation means for perturbing said stream with at least a preselected frequency and amplitude to cause said stream to form a breakpoint at which said stream become a series of discrete droplets;
   (d) droplet charging means for relatively charging selected ones of said droplets as they are formed at said breakpoint; and
   (e) synchronization means for timing said relative charging such that said selected droplets contain at least selected particles detected by said optical detection means; said synchronization means comprising:
       (i) sheath sensing means for sensing at least the light scatter characteristic of said stream at a sheath sensing point therealong subsequent to said perturbation and for producing a surface character output signal which is proportional thereto;
       (ii) surface character analysis means for producing an output signal which is at least selectively responsive to said surface character output signal; and (iii) amplitude adjustment means responsive to said surface character analysis means for adjusting said amplitude of said perturbation means for establishing and maintaining said breakpoint at said sheath sensing point.

2. The invention of claim 1 wherein said amplitude adjustment means further comprises a transducer, transducer driver, and controlled amplitude oscillator means for acting through said transducer driver on said transducer to selectively vary said amplitude of perturbation applied to said stream.

3. The invention of claim 1 wherein said surface character analysis means comprises a wave form characteristics detector generator, reference wave form characteristics setting means for generating an output signal corresponding to desired wave form characteristics of the surface character output signal when the sheath sensing point is located at said breakpoint; and an error signal generator for comparing the outputs of said reference wave form characteristic setting means and said wave form characteristic detector generator, said error signal generator comprising means for generating a proportional error signal in response to compared differences therebetween.

4. The invention of claim 1 wherein said sheath sensing means comprises a radiant energy source with respect to which the sheath stream portion is essentially translucent, and a radiant energy receptor for measuring at least the scatter of said radiant energy by said sheath stream portion and for producing an output signal proportional thereto.

5. The invention of claim 4 wherein said radiant energy source is a source of light energy.

6. The invention of claim 5 wherein said source of light energy is a helium-neon laser.

7. A method of electrostatically sorting particles comprising:
(a) establishing the flow of a continuous particle containing stream comprising at least a particle containing core stream portion and a surrounding sheath stream portion, said stream having a particle sensing point defined therealong;
(b) optically detecting said particles at least at said particle sensing point;
(c) perturbing said stream with at least a preselected frequency and amplitude to cause said stream to form a breakpoint at which said stream becomes a series of discrete droplets;
(d) relatively charging selected ones of said droplets as they are formed at said breakpoint; and
(e) synchronizing said relative charging such that said selected droplets contain at least selected particles detected in said optical detection step; said synchronizing step comprising the steps of:
(i) sensing at least the light scatter characteristics of said stream at a sheath sensing point therealong downstream from said perturbing for producing a surface character output signal which is proportional thereto;
(ii) analyzing said surface character output signal to produce an output signal which is at least selectively responsive to said surface character output signal; and
(iii) adjusting said preselected amplitude in said perturbing step in response to said selectively responsive output signal to establish and maintain said breakpoint at said sheath sensing point.

8. The invention of claim 7 wherein said step of analyzing the surface character output signal comprises the steps of generating a current surface character output waveform, generating a reference waveform setting corresponding to a desired waveform characteristic of the surface character output signal when the sheath sensing point is located at said breakpoint, and comparing said waveforms to generate an error signal proportional to the compared differences therebetween.

9. The invention of claim 7 wherein said step of sensing the light scatter characteristics of said stream comprises the steps of selecting a radiant energy source with respect to which at least the sheath stream portion is essentially translucent, focusing said radiant energy source on at least said sheath stream portion at said sheath sensing point, and measuring at least the scatter of said radiant energy caused by said sheath stream portion at said sheath sensing point to produce said surface character output signal.

10. The invention of claim 9 wherein said step of selecting said radiant energy source comprises the step of selecting a light source with respect to which said sheath stream portion is essentially translucent.

11. The invention of claim 10 wherein said step of selecting said source of light energy comprises the step of selecting a helium-neon laser, the energy output of which is essentially translucent with respect to at least said sheath stream portion.

12. An electrostatic particle sorting system, comprising:
(a) flow means for establishing the flow of a continuous particle containing stream comprising at least a particle containing core stream portion and a surrounding sheath stream portion, said stream having a particle sensing point defined therealong;
(b) particle sensing means for detecting said particles at least at said particle sensing point;
(c) perturbation means for perturbing said stream with at least a preselected frequency and amplitude to cause said stream to form a breakpoint at which said stream become a series of discrete droplets;
(d) droplet charging means for relatively charging selected ones of said droplets as they are formed at said breakpoint; and
(e) synchronization means for timing said relative charging such that said selected droplets contain at least selected particles detected by said detection means; said synchronization means comprising:
(i) sheath sensing means for sensing at least the light scatter characteristic of said stream at a sheath sensing point therealong subsequent to said perturbation and for producing a surface character output signal which is proportional thereto;
(ii) surface character analysis means for producing an output signal which is at least selectively responsive to said surface character output signal; and
(iii) amplitude adjustment means responsive to said surface character analysis means for adjusting said amplitude of said perturbation means for establishing and maintaing said breakpoint at said sheath sensing point.

13. A method of electrostatically sorting particles comprising:

(a) establishing the flow of a continuous particle containing stream comprising at least a particle containing core stream portion and a surrounding sheath stream portion, said stream having a particle sensing point defined therealong;

(b) detecting said particles at least at said particle sensing point;

(c) perturbing said stream with at least a preselected frequency and amplitude to cause said stream to form a breakpoint at which said stream becomes a series of discrete droplets;

(d) relatively charging selected ones of said droplets as they are formed at said breakpoint; and (e) synchronizing said relative charging such that said selected droplets contain at least selected particles detected in said detection step; said synchronizing step comprising the steps of:

(i) sensing at least the light scatter characteristics of said stream at a sheath sensing point therealong downstream from said perturbing for producing a surface character output signal which is proportional thereto;

(ii) analyzing said surface character output signal to produce an output signal which is at least selectively responsive to said surface character output signal; and (iii) adjusting said preselected amplitude in said perturbing step in response to said selectively responsive output signal to establish and maintain said breakpoint at said sheath sensing point.

* * * * *